(12) United States Patent
Noferini et al.

(10) Patent No.: US 11,890,172 B2
(45) Date of Patent: Feb. 6, 2024

(54) DEVICE FOR PROCESSING AND APPLYING PIECES FOR MAKING ABSORBENT ARTICLES

(71) Applicant: GDM S.p.A., Bologna (IT)

(72) Inventors: Giacomo Noferini, Castenaso (IT); Federico Tordini, Treviglio (IT); Matteo Piantoni, Albino (IT)

(73) Assignee: GDM S.P.A., Bologna (IT)

( * ) Notice: Subject to any disclaimer, the term of this patent is extended or adjusted under 35 U.S.C. 154(b) by 625 days.

(21) Appl. No.: 17/053,486

(22) PCT Filed: May 2, 2019

(86) PCT No.: PCT/IB2019/053587
§ 371 (c)(1),
(2) Date: Nov. 6, 2020

(87) PCT Pub. No.: WO2019/215547
PCT Pub. Date: Nov. 14, 2019

(65) Prior Publication Data
US 2021/0228422 A1    Jul. 29, 2021

(30) Foreign Application Priority Data

May 7, 2018    (IT) ......................... 102018000005102

(51) Int. Cl.
*A61F 13/15*        (2006.01)
*B65H 35/08*        (2006.01)

(52) U.S. Cl.
CPC .. *A61F 13/15764* (2013.01); *A61F 13/15723* (2013.01); *B65H 35/08* (2013.01); *B65H 2801/57* (2013.01)

(58) Field of Classification Search
CPC .......... A61F 13/15764; A61F 13/15723; A61F 13/15756; B65H 2801/57; B65H 35/08;
(Continued)

(56) References Cited

U.S. PATENT DOCUMENTS 5,025,910 A * 6/1991 Lasure ................. B65G 47/244
198/377.04
9,717,634 B2 * 8/2017 Tameishi .......... A61F 13/15764
(Continued)

FOREIGN PATENT DOCUMENTS

EP          1162162 A1    12/2001
JP      2010142415 A     7/2010
(Continued)

OTHER PUBLICATIONS

International Search Report and Written Opinion dated Jul. 12, 2019 from counterpart International Patent Application No. PCT/IB2019/053587.

(Continued)

*Primary Examiner* — Ghassem Alie
(74) *Attorney, Agent, or Firm* — SHUTTLEWORTH & INGERSOLL, PLC; Timothy J. Klima

(57) ABSTRACT

A device for applying pieces to absorbent articles includes a supporting shaft rotating an axis; anvils rotating about the axis; a cutting unit operating with an anvil contact surface defining a cutting station for cutting a web into pieces; pads, each having a retaining surface for a piece, are moved about the axis for conveying a piece from the cutting station to a releasing station for release onto a substrate. Each pad rotates for varying the orientation from the cutting station, where the larger side of the pad is parallel to a feed of the web, to the releasing station, where the larger side of the pad is transversal to the feed of the receiving substrate, and vice versa. Each pad translates parallel to the pad axis, away from and towards the shaft axis. Each pad has an oscillating movement about its own axis.

13 Claims, 4 Drawing Sheets

(58) Field of Classification Search
CPC .......... B65H 29/241; B65H 2106/3454; B65H 2406/3452; B65H 39/14; B65H 2301/33216; B65G 47/244; B65G 47/915; B65G 29/02; B65G 47/848; B26D 1/425; B26D 7/018
USPC .................... 83/107; 198/377, 379, 441, 450
See application file for complete search history.

(56) References Cited

U.S. PATENT DOCUMENTS

| | | | |
|---|---|---|---|
| 10,039,674 B2 * | 8/2018 | Wada | A61F 13/15764 |
| 2007/0074953 A1 * | 4/2007 | McCabe | B65G 47/848 |
| | | | 198/377.08 |
| 2008/0196564 A1 | 8/2008 | McCabe | |
| 2011/0319243 A1 * | 12/2011 | Fujita | B65H 29/241 |
| | | | 493/437 |
| 2019/0241393 A1 * | 8/2019 | McCabe | B65H 35/08 |

FOREIGN PATENT DOCUMENTS

| | | |
|---|---|---|
| JP | 2015530931 A | 10/2015 |
| WO | 2014016732 A1 | 1/2014 |
| WO | 2015079367 A1 | 6/2015 |

OTHER PUBLICATIONS

Japanese Office Action dated Jan. 6, 2023 from counterpart Japanese Patent Application No. 2020-562650.

* cited by examiner

DEVICE FOR PROCESSING AND APPLYING PIECES FOR MAKING ABSORBENT ARTICLES

This application is the National Phase of International Application PCT/IB2019/053587 filed May 2, 2019 which designated the U.S.

This application claims priority to Italian Patent Application No. 102018000005102 filed May 7, 2018, which application is incorporated by reference herein.

TECHNICAL FIELD

This invention relates to a device for processing and applying pieces for making absorbent articles.

BACKGROUND ART

In particular, this device fits into the sector for processing a continuous web intended to form separate pieces for making absorbent articles for children or adults.

For example, the above-mentioned pieces may be in the form of absorbent "pads", or elasticated belts for fastening absorbent articles, or other items.

In particular, the device disclosed divides the continuous web into single pieces, conveys the pieces obtained by dividing the continuous web to an applying station and, during that conveying, the device also varies the orientation of each piece relative to a starting configuration determined by the cutting of the web.

Usually prior art devices, of the type indicated above, comprise a plurality of anvils operating in conjunction with cutting means and a plurality of device pads, each interposed between two respective anvils.

As well as rotating about the axis of rotation of the above-mentioned drum, the pads are able to rotate on themselves in order to orient the respective piece according to a line transversal to the line of feed of the depositing web.

Moreover, during their rotation, each pad, must recover and cancel the difference which usually exists between the feed speed of the continuous web, from which the pieces are obtained, and the feed speed of the depositing web.

DISCLOSURE OF THE INVENTION

In this context the need is felt to supply a device for processing and applying pieces for making absorbent articles comprising a supporting shaft, rotating about its own axis of rotation, a plurality of anvils rotating about the axis of rotation of the shaft and a cutting unit which operates in conjunction with a respective contact surface of an anvil for defining a cutting station for cutting a continuous web for making absorbent articles in single pieces.

A plurality of pads, each having a respective retaining surface for a piece, which are moved about the axis of rotation of the shaft for conveying a respective piece from the cutting station to a releasing station for releasing it onto a receiving substrate. Each pad has a rotating movement about its own axis for varying the respective orientation from the cutting station, where the larger side of the pad is parallel to the line of feed of the continuous web, to the releasing station, where the larger side of the pad is transversal to the line of feed of the receiving substrate, and vice versa.

Each pad has a translating movement, along a line parallel to the respective axis of rotation, away from and towards the axis of rotation of the shaft.

Each pad has an oscillating movement about its own axis of oscillation.

The axis of oscillation of the pad is eccentric relative to the axis of rotation of the shaft and has a line of extension parallel to the axis of rotation of the shaft. The axis of rotation of the pad is radial relative to that axis of oscillation.

Advantageously, the absolute tangential speed that the pad of the device can reach is equal to the sum of the pad oscillation contribution and the rotational speed that the supporting shaft imparts to the pad.

BRIEF DESCRIPTION OF DRAWINGS

The invention is described below with reference to the accompanying drawings, which illustrate a non-limiting embodiment of it, and in which.

DETAILED DESCRIPTION OF PREFERRED EMBODIMENTS OF THE INVENTION

Figure 1:
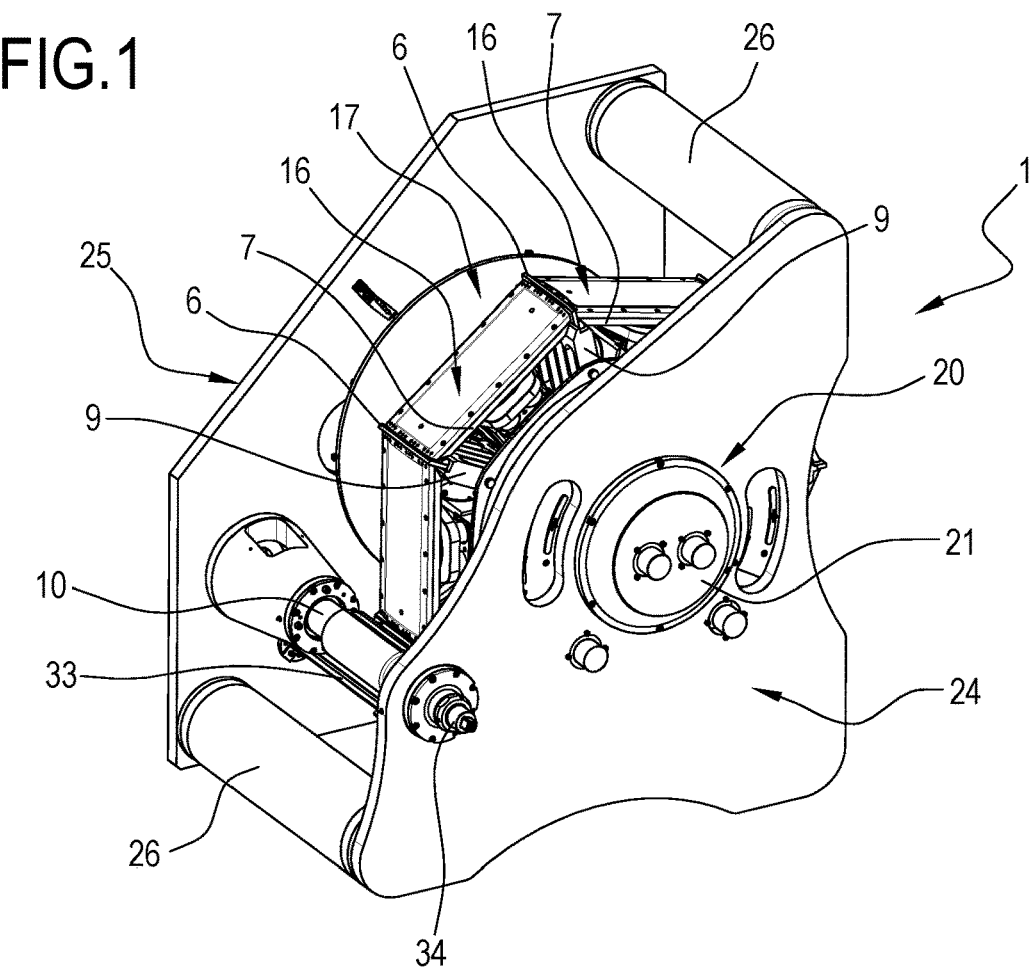
FIG. 1 is a schematic perspective view of the device according to this invention.

The numeral 1 denotes a device for processing and applying pieces 2 for making absorbent articles.

In this embodiment, the term piece 2 means an absorbent "pad" of an absorbent article 3.

That piece 2 for making articles is obtained by cutting a continuous web 4 of material for making articles which is fed to the device 1.

In this embodiment, the continuous web 4 of material for making articles comprises at least a first layer of permeable non-woven material, known as the "topsheet", a second layer of permeable non-woven material, known as the "backsheet", a core of absorbent material interposed between the first and second layers, and lateral bands made of elasticated material.

The device 1 comprises a plurality of anvils 6 rotating about an axis 13a of rotation.

Each anvil 6 has a respective contact surface, labelled 5 in the figure, for cutting the continuous web 4 into the single pieces 2.

The device 1 comprises a wheel 8 for supporting the anvils 6.

The device 1 comprises a supporting shaft 13 for supporting at least the wheel 8, rotating about its own axis 13a of rotation.

The wheel 8 and the anvils 6 supported by it are also rotatable about the axis 13a of rotation of the shaft 13.

The wheel 8 comprises a plurality of spokes 9, each of which on its respective free end 9a supports an anvil 6.

The spokes 9 are positioned equidistant from each other and, consequently, so are the anvils 6 supported by them.

Considering the fact that each anvil 6 is supported by a respective spoke 8, the anvils 6 maintain their radial distance relative to the axis 13*a* of rotation.

With regard to that, it should be noticed that the cutting step for the continuous web 4 is closely linked to the diameter defined by the free ends 9*a* of the spokes 9 of the wheel 8 which support the anvils 6, since those ends 9*a* define the vertices of a regular polygon, the length of whose sides coincides with the desired cutting step.

The device 1 comprises a cutting unit 10, preferably comprising a shaft 34, rotating about its own axis 34*a*, equipped with one or more cutting edges 33, which operate in conjunction with a respective contact surface 5 of the anvil 6 for cutting the continuous web 4 into pieces 2.

The cutting unit 10 and an anvil 6 operating in conjunction with it define a cutting station 11 for cutting the continuous web 4.

The continuous web 4 is separated into pieces 2 by impact cutting between the cutting edge 33 of the cutting unit 10 and the blade stop, the contact surface 5 of the anvil 6, which make contact at a theoretical tangent point between the reference circumferences of the shaft of the cutting unit 10 and of the wheel 8 which has spokes 9.

The wheel 8 which has spokes 9 and the shaft of the cutting unit 10 are moved by respective independent transmissions, which are not illustrated.

An electronic control system 35, which uses sensors configured to detect the synchronised passage of the cutting edge 33 of the cutting unit 10 and of the single anvil 6, is configured to maintain the correct engagement between the cutting edge 33 of the cutting unit 10 and the contact surface 5 of the anvil 6.

Given the precision required for cutting the continuous web 4 and for guaranteeing an acceptable length of service of the cutting edge 33 of the cutting unit 10 and of the surface 5 of the anvil 6 it is essential to avoid or contain within strict acceptability limits the thermal deformations caused by the rolling of main bearings 32 interposed between the wheel 8 which has spokes 9 and the supporting shaft 13.

There are cooling means 31 in the inner zone of the shaft 13 corresponding to the positioning of the main bearings 32.

It is worth emphasising that the precision of the cut is guaranteed by the tight working tolerances of the mechanical components and by the rolling precision of the main bearings 32 with which the wheel 8 is constrained to the supporting shaft 13.

The device 1 comprises a front plate 24 and a rear plate 25 which are connected to each other by at least three columns 26 to form a rigid framework or frame of the device 1.

The shaft 13 is constrained to the front plate 24 and to the rear plate 25 by its ends, as shown in FIG. 1.

The device 1 comprises a plurality of pads 7 each of which has a respective surface 16 for retaining and releasing a respective piece 2.

Each pad 7 is positioned between two respective anvils 6, which are consecutive considering the positioning of the anvils 6 relative to each other on the supporting wheel 8.

The pads 7 allow the retaining and conveying of a respective piece 2, obtained by cutting the continuous web 4, from the cutting station 11 to a releasing station 27 for releasing the piece 2.

In order to convey the pieces 2 from the cutting station 11 to the releasing station 27, the pads 7 of the device are movable about the axis 13*a* of rotation of the anvils 6.

Figure 2:
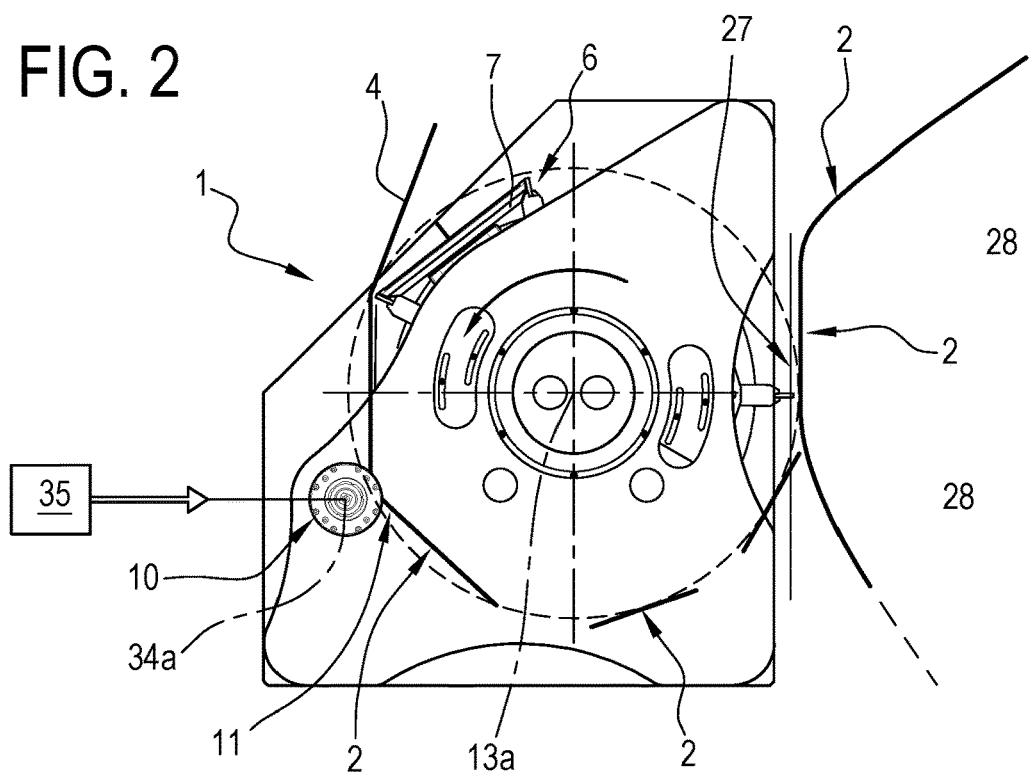
FIG. 2 is a schematic front view of the device according to this invention.

At the releasing station 27, each pad 7 deposits the respective piece 2 on a receiving substrate 28, as shown in FIG. 2.

In particular, according to the embodiment of this invention, the substrate is composed of two continuous webs, which are fed parallel to each other, on which the pieces 2 are deposited according to a predetermined step.

The pieces 2 are deposited by the pad 7 according to a line transversal to the line of feed of the continuous webs, using a method defined as "cross direction".

In order to release the piece 2 with a "cross direction" orientation relative to the receiving substrate 28, each pad 7 varies its orientation from the cutting station 11 to the releasing station 27 for releasing the piece 2, and vice versa, by rotating about a respective axis 7*a* of rotation.

At the cutting station 11, each pad 7 of the device 1 is positioned according to a main line of extension which is the same as the line of feed of the continuous web 4, as shown in the FIG. -.

At the releasing station 27, each pad 7 of the device 1 is positioned according to a main line of extension transversal to the line of feed of the receiving substrate 28, as shown in the FIG. -.

The variation in the orientation of each pad 7 from the cutting station 11 to the releasing station 27 is performed by means of the rotating movement of the pad 7 about its own axis 7*a* of rotation.

The term axis of rotation 7*a* of the pad 7 means an axis 7*a* normal to the respective surface 16 for retaining and releasing the piece 2.

In particular, from the cutting station 11 to the releasing station 27, each pad 7 rotates through 90° about its own axis 7*a* of rotation.

From the releasing station 27 to the cutting station 11, each pad 7 rotates through a further 90° about its own axis 7*a* of rotation for positioning itself again according to a main line of extension which is the same as the line of feed of the continuous web 4.

Each pad 7 also has a translating movement away from and towards the axis 13*a* of rotation of the anvils 6.

That translating movement is parallel to the respective axis 7*a* of rotation of the pad 7, normal to the retaining surface 16 of the pad 7.

From the cutting station 11 to the releasing station 27, each pad 7, during the rotation about its own axis 7*a*, translates away from the axis 13*a* of rotation of the anvils 6 so as to prevent a collision between the pad 7 and the anvils 6 between which it is positioned.

At the releasing station 27, the pad 7 is in the position furthest away from the axis 13*a* of rotation of the anvils 6.

In the position furthest away from the axis 13*a* of rotation of the anvils 6, the surface 16 of the pad 7 is positioned above the anvils 6 between which it is placed.

From the releasing station 27 to the cutting station 11, each pad 7, during the rotation about its own axis 7*a*, translates towards the axis 13*a* of rotation of the anvils 6.

At the cutting station 11, the pad 7 is in the position closest to the axis 13*a* of rotation of the anvils 6.

In the position closest to the axis 13*a* of rotation of the anvils 6, the surface 16 of the pad 7 is aligned with the surface 5 of the anvils 6 between which it is placed.

It should be noticed that each pad 7 of the device 1 can perform the movement about the axis 13*a* of rotation of the supporting shaft 13, as well as the anvils 6, a rotating movement about its own axis 7*a* of rotation and a translating movement along that axis 7*a*.

Relating to the movements of translating and of rotating about its own axis 7a, each pad 7 has a respective movement unit 14 comprising kinematic means 30 configured for transmitting to the pad 7 the translating movement, away from and towards the axis of rotation 13a of the shaft 13, and the rotating movement of the pad 7 about its own axis of rotation 7a.

Figure 4:
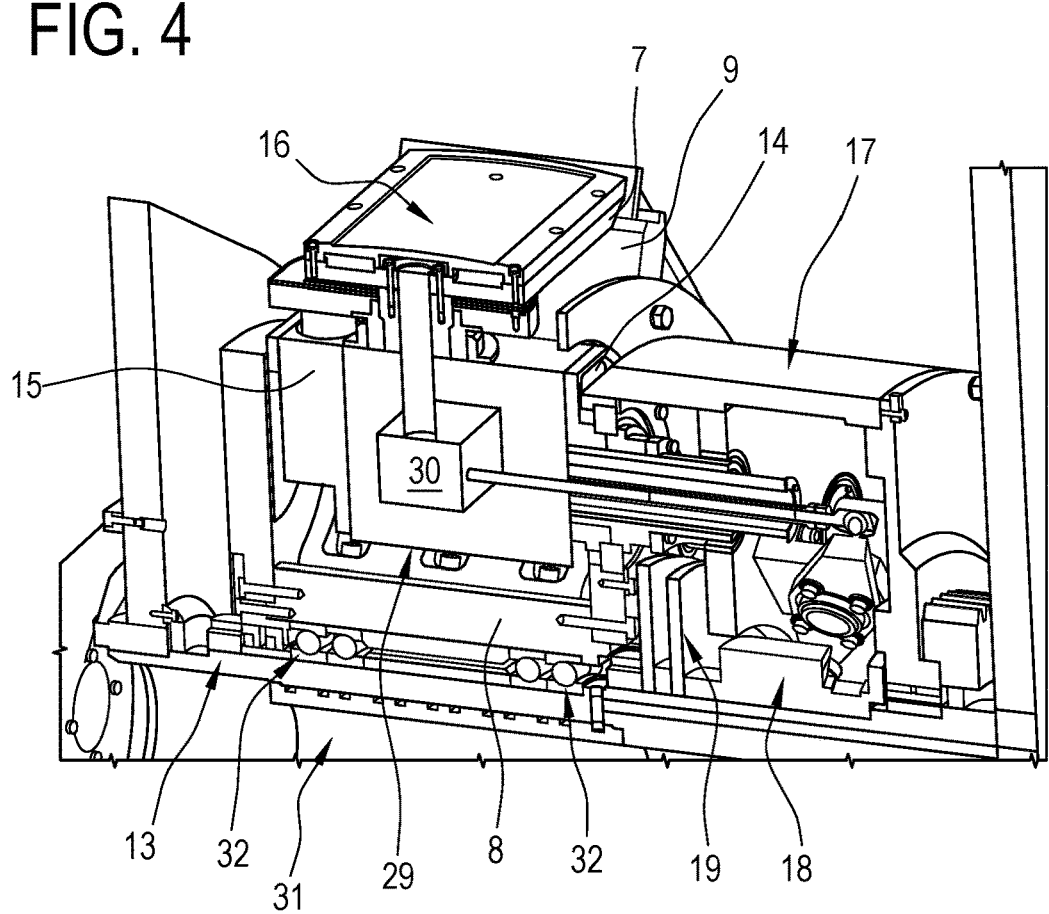
FIG. 4 is a schematic cross-section of the device of FIG. 1.

Each movement unit 14 has a respective casing 29, preferably monolithic, inside which the kinematic means 30 are housed immersed in a lubricating substance, as shown in FIG. 4.

The casing 29 is below the respective pad 7.

Each movement unit 14 comprises a respective vacuum distributor 15 for the surface 16 of the pad 7.

The vacuum distributor 15 is connected to the above-mentioned casing 29.

Figure 3:
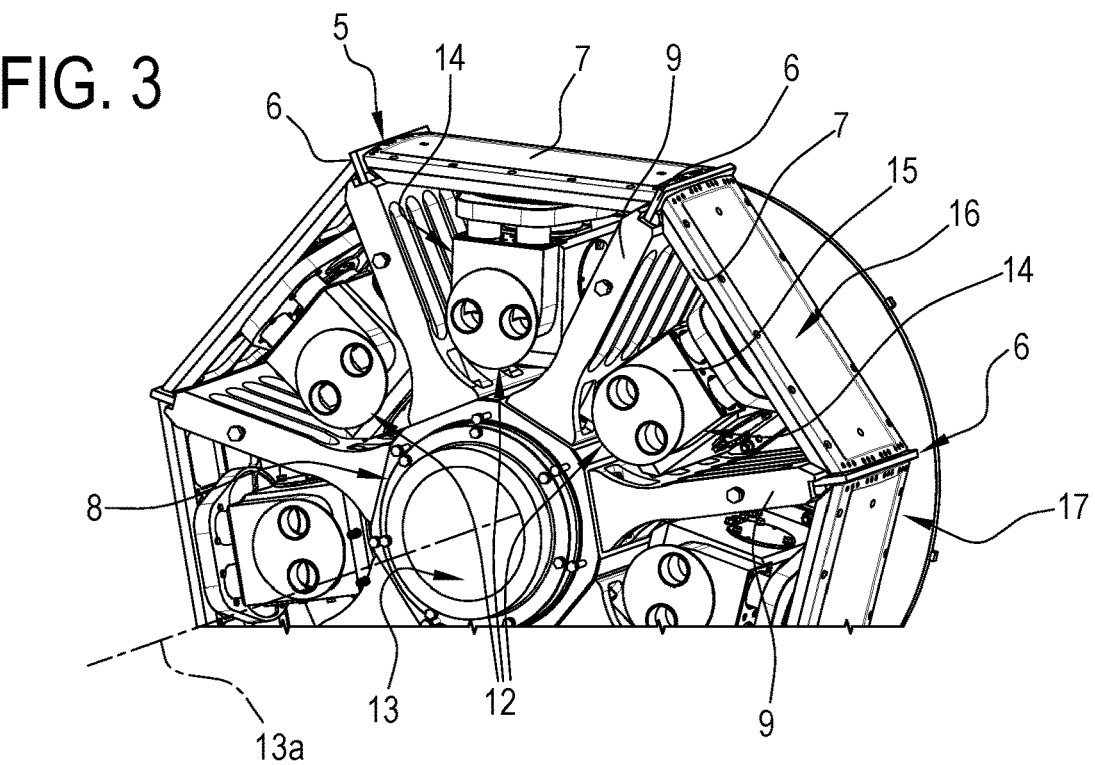
FIG. 3 is a schematic perspective view of a detail of FIG. 1 with some parts cut away to better illustrate others.

The movement unit 14 of a respective pad 7 is positioned in a housing compartment 12 defined by the gap between spokes 9, one after the other, supporting the anvils 6 between which the pad 7 is interposed, as shown in FIG. 3.

It should be noticed that, in this sense, the number of pads 7 of the device 1, and of the respective movement units 14, is equal to the number of spokes 9 of the rotatable wheel 8.

According to this invention, each pad 7 has an oscillating movement about a respective axis 14a of oscillation.

That axis 14a of oscillation is an axis parallel to the axis of rotation 13a of the supporting shaft 13 and eccentric relative to the axis of rotation 13a of the supporting shaft 13.

Figure 6:
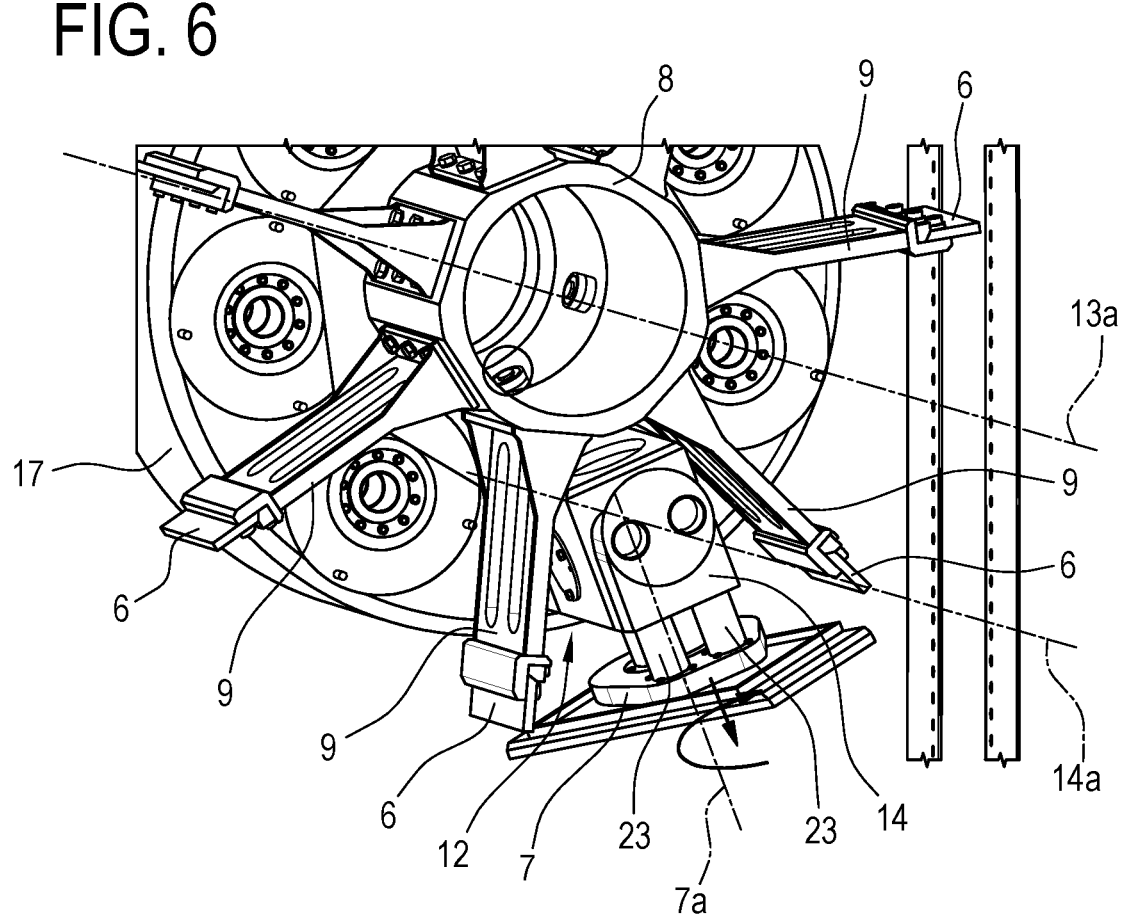
FIG. 6 is a schematic front view of a further detail of the device of FIG. 1.

The axes 14a of oscillation of the pads 7 of the device 1 are positioned along the same ideal circle having as its centre the axis 13a of rotation of the supporting shaft 13, as shown in FIG. 6.

It should be noticed that the axis 7a of rotation of each pad 7 is a radial axis relative to the axis 14a of oscillation of the pad 7.

Moreover, the translating movement of the pad 7 is also away from and towards the respective axis 14a of oscillation, again along the line of the axis 7a of rotation.

The device 1 comprises a drum 17 supporting and housing the movement units 14.

The drum 17 is mounted on the supporting shaft 13 and is rotatable about the axis 13a of the shaft 13.

The spokes 9 of the wheel 8 are constrained to the drum 17, driving its rotation about the axis 13a of the shaft 13 by means of the wheel 8 supporting the anvils 6.

Therefore, the pads 7 with the respective movement unit 14 are driven to move about the axis 13a of rotation of the supporting shaft 13.

Housed inside the drum 17 there are first cam means 18, in particular in the form of a drum cam, used for imparting, by means of the kinematic means 30 of the respective movement unit 14, the translating movement of each pad 7.

The first cam means 18 allow the production, simultaneously with the translating movement, of the rotating movement of the pad 7 about its own axis 7a of rotation.

Housed inside the drum 17 there are second cam means 19, in particular in the form of conjugate cams, for imparting the oscillating movement to the movement unit 14 and consequently to the pad 7 constrained to it, about the respective axis 14a of rotation.

In this way, the local speed of rotation of each pad 7 about the axis 14a of oscillation, added to the rotational driving speed of the wheel 8 supporting the anvils 6, gives the retaining and releasing surface 16 of a respective pad 7 an absolute tangential speed which it is possible to modulate by means of the profile of the second can means 19.

Advantageously, the absolute tangential speed that the pad 7 of the device 1 succeeds in reaching, adding together the contribution of the oscillation of the pad 7 about the axis 14a of oscillation and the rotational driving speed of the wheel 8, is established in relation to the feed speed of the receiving substrate 28 for the pieces 2 in the releasing station 27.

Similarly to the movement units, the drum 17 has a "closed" casing structure in which the means housed in it are in a bath of lubricating substance.

Regarding the suction system of the pads 7 for retaining and releasing the piece 2 on the respective retaining surface 16, the device 1 comprises a front manifold 20 for distributing the vacuum to the distributors 15 of each pad 7.

The front manifold 20 comprises a short-circuited double duct 21 extending for a suitable arc of a circle at least equal to that subtended between the cutting station 11 and the releasing station 27.

At the cutting station 11 and the releasing station 27 there are suitable adjusting blocks for modulating the length of the ducts 21.

A vacuum is created in those ducts 21, which are parallel to each other, by suction through the inside of the supporting shaft 13 of the wheel 8.

The vacuum is shared two ways for each distributor 15 of a respective pad 7.

With reference to each pad 7, each distributor 15 comprises two independent ducts 22 for conveying the vacuum from the front manifold 20 to each pad 7.

Each distributor 15 has telescopic sections 23 engaged in the suction ducts 22.

The telescopic sections 23, positioned in the part below each pad 7, allow the continuity of the suction ducts 22 to be maintained during the translating movement of the pad 7.

Figure 5:
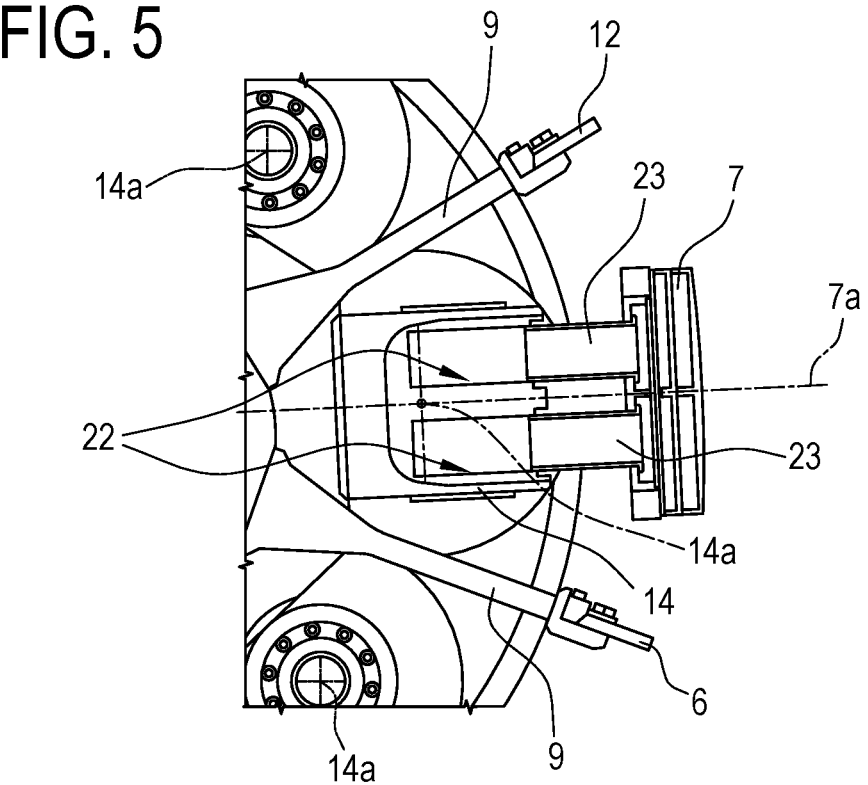
FIG. 5 is a schematic front view of a detail of FIG. 1 with some parts cut away to better illustrate others.

FIG. 5 shows that when the pad 7 is in the position furthest from the respective axis 14a of oscillation or from the axis 13a of rotation of the supporting shaft 13, the telescopic sections 23 are translated outside the suction ducts 22 of the distributor 15.

Inside each pad 7 there are two separate chambers, each of which extends mainly along a line longitudinal to the pad 7, each chamber having an opening in communication with the respective distributor 15.

Interposed between the opening of each chamber and the distributor 15 there is a disk, not illustrated, having an opening which is selectively obstructed based on the relative movements of the pad 7 from the cutting station 11 to the releasing station 27.

In particular, at the releasing station 27, with the pad 7 oriented transversally, sequential shutting off of the suction in the chambers is achieved, improving the gradualness of the piece 2 releasing step.

At the cutting station 11, when the pad 7 is oriented longitudinally, there is no need for gradual starting of the suction in the pad 7, since it is not necessary to start the suction before the continuous web 4 is completely wrapped on the pad 7.

Considering the device 1 in use, the continuous web 4 wraps around the device 1, in particular around the pads 7 which are oriented with their larger side parallel to the line of feed of the continuous web 4.

The pads 7 which receive the continuous web 4 have a constant speed which is identical to the driving speed at which the anvil 6 supporting wheel 8 drives the anvils 6.

Only after the continuous web 4 adheres to the surface 16 of at least one pad 7, the respective distributor 15 of the pad 7 comes into action, allowing the continuous web 4 to be retained adhering to the surface 16 of the pad 7 in such a way as to convey it to the cutting station 11.

At the cutting station 11, the continuous web 4 is divided into single pieces 2 and the piece 2 separated from the continuous web 2 remains constrained to the pad 7 by means of the suction.

Upstream of the cut piece 2, the continuous web 4 remains adhering to the consecutive pad 7 as previously described.

Figure 7:
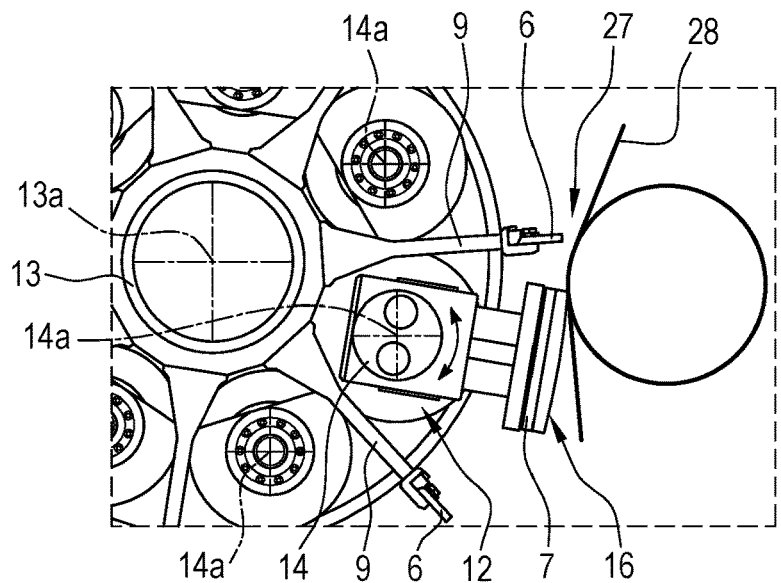
FIGS. 7 to 9 are schematic front views of a detail of the device according to this invention during a step of releasing a separate piece onto a receiving substrate.
Figure 8:
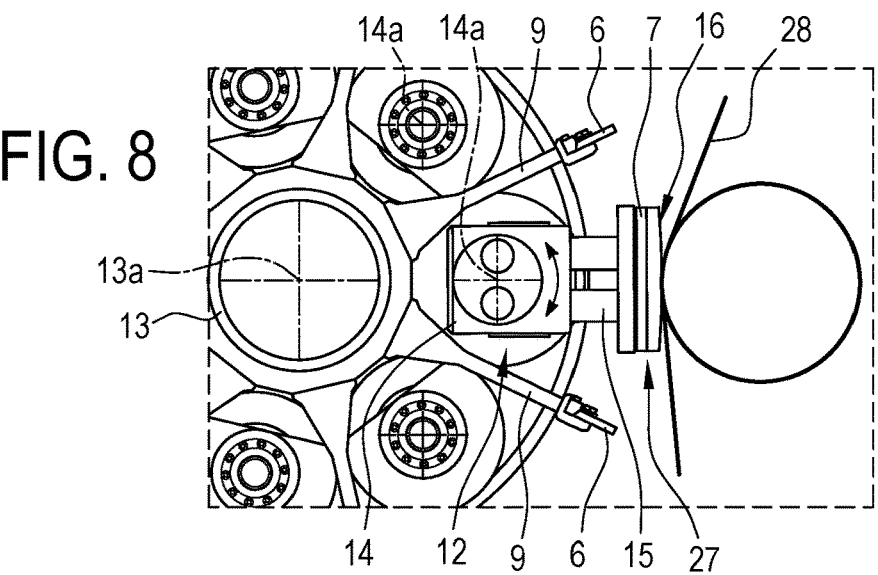
Figure 9:
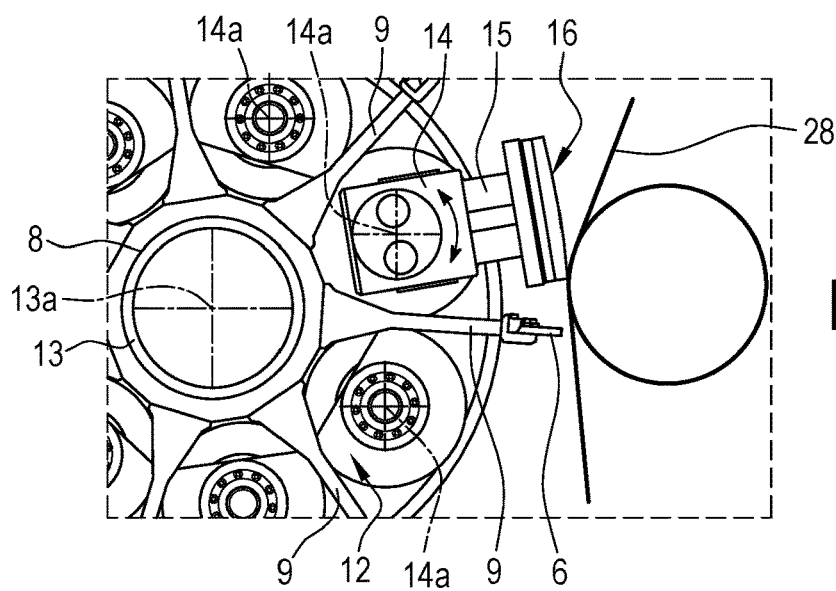

Downstream of the cutting station 11, the kinematic means 30 of the movement unit 14 of the pad 7, which conveys the piece 2 towards the releasing station 27 by means of the movement about the axis 13a of the supporting shaft 13, are operated by the second cam means 19, as shown in FIGS. 7 to 9.

The pad 7 translates away from the axis 14a of oscillation of the respective movement unit 14 along a line that is radial relative to that axis 14a and, simultaneously, rotates about its own axis 7a of rotation.

The rotation of the pad 7 about its own axis 7a of rotation is equal to an angle of 90° in such a way that the surface 16 of the pad 7 is positioned according to a line transversal to the line of feed of the receiving substrate 28 for receiving the piece 2.

In other words, at the releasing station 27, the pad 7 is rotated through 90° relative to the configuration adopted at the cutting station 11.

As previously emphasised, the correction of the speed of the pad 7, without which the latter would remain rigidly constrained to the driving motion, at constant speed, of the wheel 8 supporting the anvils 6, is obtained by superposing on the uniform angular motion a rotation about the axis 14a of oscillation of the respective movement unit 14.

That oscillation may be in the same direction as the direction of rotation of the supporting shaft 13 or in the opposite direction to the direction of rotation of the supporting shaft 13.

Following application of the piece 2 to the substrate 28, the kinematic means 30 of the movement unit 14 of the pad 7 are operated by the second cam means 19 for performing the movements of rotation of the pad 7 about its own axis 7a and translation towards the axis 14a of rotation of the movement unit 14 for again orienting the pad 7 in such a way as to receive the continuous web 4.

With reference to what is indicated in this description, the device 1 disclosed allows a continuous web 4 to be separated into separate pieces 2 (absorbent pads, or inserts of nappies or incontinence pants), said pieces 2 to be picked up and conveyed by means of suitable gripping elements, the device pads 7 with the aid of a suitable suction system, rotating through 90°, spacing out and depositing each piece 2 on a suitable substrate 28 for depositing which is in turn conveyed by a transfer wheel or by a flat conveyor.

The device 1 as described has been devised to satisfy, in particular, the need to perform the process of application of a piece in the form of an absorbent pad for nappies or pants, in particular with production rates of up to 800 ppm.

The main advantages of the device 1 are the integration, in a single device 1, of not just the rotation and size-related spacing of the piece 2, but also the process of cutting the continuous web 4 into separate pieces 2, thereby reducing any risks and difficulties which could arise from management of a further transfer of material if cutting were performed by a theoretical dedicated cutting unit positioned upstream.

A further advantage is the reduction of the frequency of maintenance work thanks to the configuration of the individual movements units 14 of the pad 7 and of the drum 17 with "fully closed" casing, which protects the latter from contamination caused by contaminating elements from the production process, such as cellulose fibres or SAP, and, vice versa, prevents the products being made from being contaminated by the lubricating substance present in the casing.

The invention claimed is:

1. A device for processing and applying pieces for making absorbent articles comprising:
    a supporting shaft rotating about an axis of rotation;
    a plurality of anvils rotating about the axis of rotation of the shaft each of the anvils including a respective contact surface;
    a cutting unit including at least one cutting edge operating in conjunction with each respective contact surface for defining a cutting station for cutting a continuous web into single pieces for making absorbent articles;
    a plurality of pads, each including a respective retaining surface for a respective one of the pieces, which are moved about the axis of rotation of the shaft for conveying the respective one of the pieces from the cutting station to a releasing station for releasing the respective one of the pieces onto a receiving substrate;
    each of the pads being provided with a rotating movement about a pad axis thereof for varying a respective orientation of each of the pads from the cutting station, where a larger side of the each of the pads is parallel to a first line of feed of the continuous web, to the releasing station, where the larger side of each of the pads is transversal to a second line of feed of the receiving substrate, and vice versa;
    each of the pads being provided with a translating movement, along a line parallel to the respective pad axis, away from and towards the axis of rotation of the shaft;
    each of the pads being provided with an oscillating movement about a respective axis of oscillation thereof; the respective axis of oscillation being eccentric relative to the axis of rotation of the shaft and having a line of extension parallel to the axis of rotation of the shaft; the pad axis being oriented radially relative to the axis of oscillation;
    for each of the pads, a connected respective movement unit comprising a respective kinematic device configured for transmitting to each of the pads the translating movement, away from and towards the axis of rotation of the shaft, and the rotating movement of each of the pads about the respective pad axis; each movement unit oscillating about the respective axis of oscillation.

2. The device according to claim 1, and further comprising, a wheel, mounted on the shaft, the wheel comprising a plurality of spokes each of which supports a respective one of the anvils; the respective movement unit being positioned in a respective housing compartment defined by a gap between an adjacent two of the spokes.

3. The device according to claim 2, and further comprising:
    main bearings interposed between the wheel and the shaft; and
    a cooling device in an inner zone of the shaft corresponding to a positioning of the main bearings.

4. The device according to claim 2, and further comprising a drum supporting and housing the respective movement units; the spokes of the wheel being constrained to the drum and driving its-rotation of the drum about the axis of the shaft by the wheel.

5. The device according to claim 4, and further comprising a first cam device housed inside the drum, used for imparting, by the kinematic device of each movement unit, the translating movement.

6. The device according to claim 5, wherein the drum has a closed casing structure and the first and the second cam devices are positioned in the closed casing structure, immersed in a lubricating substance.

7. The device according to claim 5, wherein the first cam device is a drum cam.

8. The device according to claim 4, and further comprising a second cam device housed inside the drum for imparting the oscillating movement.

9. The device according to claim 8, wherein the second cam device includes conjugate cams.

10. The device according to claim 1, wherein the respective movement unit has a respective casing, in which the respective kinematic device is housed immersed in a lubricating substance; the respective casing being below the each of the pads and being relatively fixed relative to the each of the pads during only the rotating movement and translating movement.

11. The device according to claim 1, and further comprising an electronic control system configured for maintaining a correct engagement between the at least one cutting edge and the anvils at the cutting station.

12. The device according to claim 1, wherein the respective movement unit comprises:
   a respective vacuum distributor for the respective retaining surface; each respective vacuum distributor comprising two ducts which are independent of each other,
   respective telescopic sections movable towards an outside and an inside of the two ducts during the translating movement.

13. The device according to claim 12, and further comprising:
   two separate chambers inside each of the pads, each of the two separate chambers extending mainly along a line longitudinal to the each of the pads and having pad an opening in communication with a respective one of the two ducts; and
   a selective closing device configured to obstruct each opening during the relative movements of the pad from the cutting station to the releasing station.

* * * * *